(12) United States Patent
Janssen et al.

(10) Patent No.: US 6,451,802 B1
(45) Date of Patent: Sep. 17, 2002

(54) S-OXIDE LIPID LOWERING COMPOUNDS

(75) Inventors: Cornelus Gerardus Maria Janssen, Vosselaar; Peter Walter Maria Roevens, Malle; Jozef Bertha August Thijssen, Kasterlee, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/857,838

(22) PCT Filed: Dec. 14, 1999

(86) PCT No.: PCT/EP99/10065

§ 371 (c)(1),
(2), (4) Date: Jun. 8, 2001

(87) PCT Pub. No.: WO00/37463

PCT Pub. Date: Jun. 29, 2000

(30) Foreign Application Priority Data

Dec. 22, 1998 (EP) .............................. 98204410

(51) Int. Cl.[7] .................. A61K 31/496; C07D 405/14; C07D 417/14
(52) U.S. Cl. ........................... 514/254.02; 514/254.07; 544/366; 544/367; 544/370
(58) Field of Search ................. 544/366, 367, 544/370; 514/254.02, 254.07

(56) References Cited

U.S. PATENT DOCUMENTS 5,929,075 A * 7/1999 Heeres et al. ............... 514/252

FOREIGN PATENT DOCUMENTS

WO      WO 96/13499 A1      5/1996

* cited by examiner

Primary Examiner—Emily Bernhardt
(74) Attorney, Agent, or Firm—Ellen Ciambrone Coletti

(57) ABSTRACT

The present invention relates to compounds of formula (I)

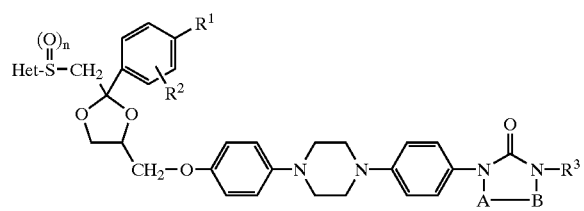

the N-oxides, the stereochemically isomeric forms thereof, and the pharmaceutically acceptable acid addition salts, wherein n is 1 or 2, $R^1$ is hydrogen, $C_{1-6}$alkyl or halo; $R^2$ is hydrogen or halo; $R^3$ is $C_{1-8}$alkyl or $C_{3-6}$cycloalkyl; Het is an optionally substituted triazole, imidazole, or thiazole; and —A—B— is a bivalent radical of formula —CH=CH—, —N=CH—, —CH=N—, wherein optionally one of the hydrogen atoms is replaced by $C_{1-4}$alkyl; having apolipoprotein B inhibiting activity and concomitant lipid lowering activity. Processes for preparing said products, formulations comprising said products and their use as a medicine are disclosed, in particular for treating disorders caused by an excess of very low density lipoproteins (VLDL) or low density lipoproteins (LDL), and especially disorders caused by the cholesterol associated with said VLDL and LDL, such as, for example, hyperlipidemia, obesitas or atherosclerosis.

9 Claims, No Drawings

S-OXIDE LIPID LOWERING COMPOUNDS

CROSS REFERENCE TO RELATED APPLICATION

This application is the national stage of Application No. PCT/EP99/10065, filed Dec. 14, 1999 which application claims priority from EP 98204410.9, filed Dec. 22, 1998.

The present invention is concerned with novel S-oxide derivatives having apolipoprotein B inhibiting activity and concomitant lipid lowering activity. The invention further relates to methods for preparing such compounds, pharmaceutical compositions comprising said compounds as well as the use as a medicine of said compounds.

WO-96/13499, published on May 9, 1996, discloses structurally related heteroaryl substituted 1,3-dioxolan-4-yl-methoxyphenyl-1-piperazinyl-phenyl-2,4-dihydro-2-alkyl-3H-1,2,4-triazol-3-one derivatives having apolipoprotein B inhibiting activity and concomitant lipid lowering activity and their use in the treatment of patients suffering from hyperlipidemia. In particular, WO-96/13499 discloses (−)-[2S-[2α,4α(S*)]]-4-[4-[4-[4-[[-2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one as compound 40. Said compound 40 of WO-96/13499 is referenced to in this application as "compound A".

The compounds of the present invention differ from the cited art-known compounds structurally, by the presence of an oxidized sulfur moiety.

Unexpectedly, compared to the structurally closest art compound, i.e. compound A, the compounds of the present invention have more favourable pharmacokinetic properties: the mean plasma concentrations of the present compounds when administered chronically are more constant and also the present compounds at least partially avoid a "first-pass" effect.

Said compound A undergoes extensive metabolisation when it passes the liver resulting in plasma levels that are dependent upon the metabolism of each treated individual. The plasma levels of compund A differ inter-individually and therefore for each subject to be treated the exact dosage and frequency of administration has to be determined individually to compensate for said individual-dependent metabolism.

The compounds of the present invention at least partially avoid the first-pass effect thereby lowering the need to adjust the exact dosage and frequency of administration for each treated subject individually thus giving improved patient compliance.

The present invention concerns compounds of formula (I)

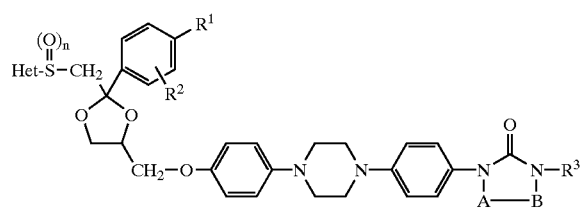

(I)

the N-oxides, the stereochemically isomeric forms thereof, and the pharmaceutically acceptable acid addition salts, wherein n is 1 or 2;
$R^1$ is hydrogen, $C_{1-6}$alkyl or halo;
$R^2$ is hydrogen or halo;
$R^3$ is $C_{1-8}$alkyl or $C_{3-6}$cycloalkyl;
Het is a radical of formula

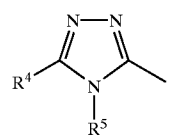 (a-1)

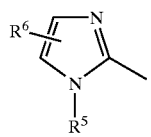 (a-2)

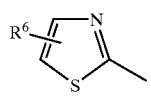 (a-3)

wherein
$R^4$ is hydrogen, $C_{1-4}$alkyl, trifluoromethyl, amino or hydroxy;
$R^5$ is hydrogen or $C_{1-4}$alkyl;
$R^6$ is hydrogen or $C_{1-4}$alkyl; and
—A—B— is a bivalent radical of formula

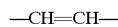 (b-1)

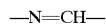 (b-2)

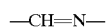 (b-3)

wherein optionally one of the hydrogen atoms is replaced by $C_{1-4}$alkyl.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{1-8}$alkyl defines $C_{1-6}$alkyl and the higher homologues thereof containing 7 or 8 carbon atoms such as, for example, heptyl or octyl and the branched isomers thereof; $C_{3-6}$cycloalkyl is generic to cyclopropyl, cyclobutyl, cyclopentyl and cyclohexyl.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of form nitrogen atom is oxidized to the N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' being equivalent to 'chirally pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

The terms cis and trans are used herein in accordance with Chemical Abstracts nomenclature and refer to the position of the substituents on a ring moiety, more in particular on the dioxolane ring in the compounds of formula (I). For instance, when establishing the cis or trans configuration of the dioxolane ring in a radical of formula (I), the substituent with the highest priority on the carbon atom in the 2 position of the dioxolane ring, and the substituent with the highest priority on the carbon atom in the 4 position of the dioxolane ring are considered (the priority of a substituent being determined according to the Cahn-Ingold-Prelog sequence rules). When said two substituents with highest priority are at the same side of the ring then the configuration is designated cis, if not, the configuration is designated trans.

All compounds of formula (I) have at least 2 stereogenic centers as indicated with an asterisk as indicated below. In the sulfoxides of formula (I-a) an additional stereogenic center is present, while the sulfones of formula (I-b) do not have said additional stereogenic center.

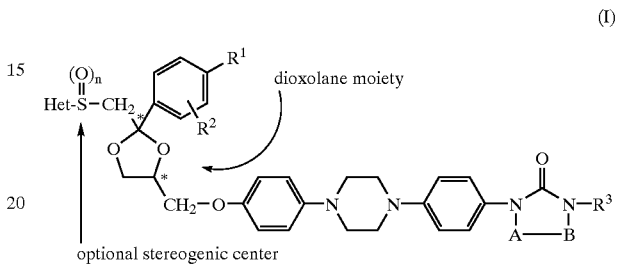

(I)

The absolute stereochemical configuration of some compounds of formula (I) and of intermediates used in their preparation, was not experimentally determined. In those cases the stereochemically isomeric form which was first isolated is designated as "A" and the second as "B", without further reference to the actual stereochemical configuration. However, said "A" and "B" isomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction.

For example, compound 1 having the stereochemical descriptor [2S-[2α,4α(S*)]] denotes the enantiomerically pure compound having the absolute configuration as depicted below, and is further characterized by its optical rotation being $[\alpha]_D^{20} = -32.05°$ (c=0.5% in N,N-dimethylformamide).

compound 1

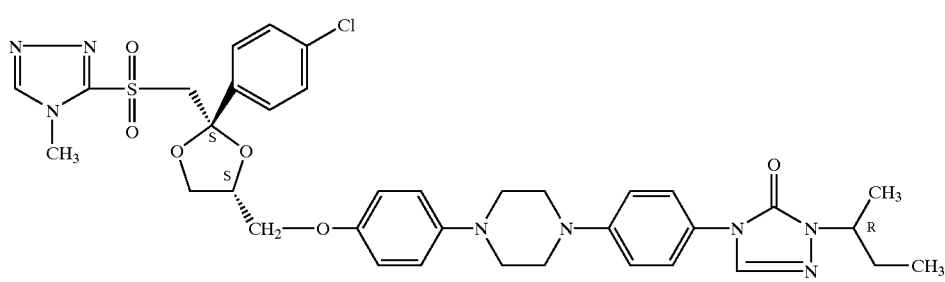

Interesting compounds are those compounds of formula (I) wherein the bivalent radical —A—B— is a radical of formula —CH=N— (b-3).

Particular compounds are those compounds of formula (I) wherein $R^1$ is halo, $R^2$ is hydrogen, $R^3$ is $C_{1-4}$alkyl and Het is (a-1) wherein $R^4$ is hydrogen and $R^5$ is $C_{1-4}$alkyl.

More particular compounds are those particular compounds of formula (I) wherein the bivalent radical —A—B— is (b-3).

Preferred compounds of formula (I) are the compounds of formula (I) wherein the dioxolane moiety has the (2S-cis) configuration.

More preferred compounds of formula (I) are those preferred compounds wherein $R^1$ is halo, $R^2$ is hydrogen, $R^3$ is $C_{1-4}$alkyl and Het is (a-1) wherein $R^4$ is hydrogen and $R^5$ is methyl.

Most preferred compounds are

[2S-[2α,4α(S*)]]-4-[4-[4-[4-[[2-(4-chloropheny)-2-[[(4-methyl-4H-1,2,4-triazol-3-yl)sulfonyl]methyl]-1,3-dioxlan-4-yl]methoxy]phenyl]-1-piperazinyl]phenyl]-2,4-dihydro-2-(1-methylpropyl)-3H-1,2,4-triazol-3-one;

[2S-[2α(A),4α(S*)]]-4-[4-[4-[4-[[2-(4-chlorophenyl)-2-[[(4-methyl-4H-1,2,4-triazol-3-yl)sulfinyl]methyl]-1,3-dioxolan-4-yl]methoxy]phenyl]-1-piperazinyl]phenyl]-2,4-dihydro-2-(1-methylpropyl)-3H-1,2,4-triazol -3-one; and [2S-[2α(B),4α(S*)]]-4-[4-[4-[[2-(4-chlorophenyl)-2-[[(4-methyl -4H-1,2,4-triazol-3-yl) sulfinyl]methyl]-1,3-dioxolan-4-yl]methoxyl]phenyl]-1-piperzinyl]phenyl]-2,4-dihydro-2-(1-methylpropyl)-3H-1,2,4-triazol-3-one; or a pharmaceutically acceptable addition salt thereof.

The compounds of the present invention can generally be prepared by reacting an intermediate of formula (III) wherein W is an appropriate leaving group such as, for example, halo, e.g. fluoro, chloro, bromo, iodo, or W may also be a sulfonyloxy group, e.g. methanesulfonyloxy, benzenesulfonyloxy, trifluoromethanesulfonyloxy and the like reactive leaving groups, with an intermediate of formula (II). The reaction can be performed in a reaction-inert solvent such as, for example, tert-butanol, acetonitrile or tetrahydrofuran, and optionally in the presence of a suitable base such as, for example, diisopropylamine, triethylamine, sodium carbonate, potassium carbonate, or calciumoxide. Stirring may enhance the rate of the reaction. The reaction may conveniently be carried out at a temperature ranging between room temperature and the reflux temperature of the reaction mixture and, if desired, the reaction may be carried out in an autoclave at an increased pressure.

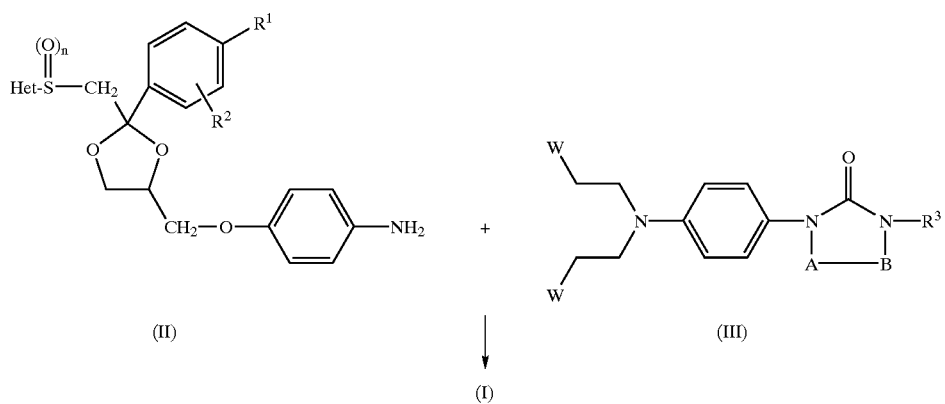

Compounds of formula (I-a), defined as compounds of formula (I) wherein n=1, can be converted to compounds of formula (I-b), defined as compounds of formula (I) wherein n=2, using art-known S-oxidation reactions.

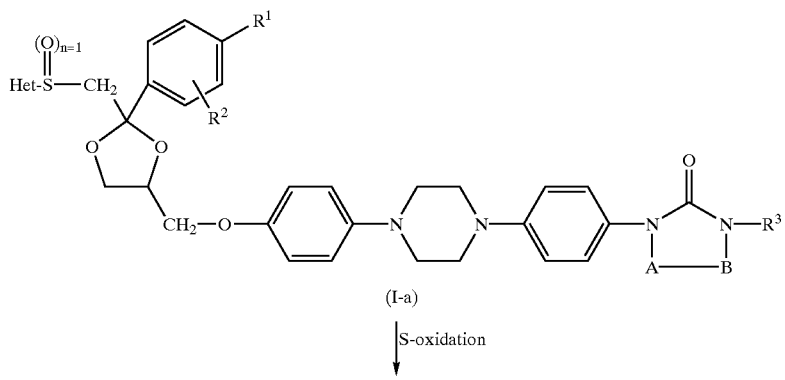

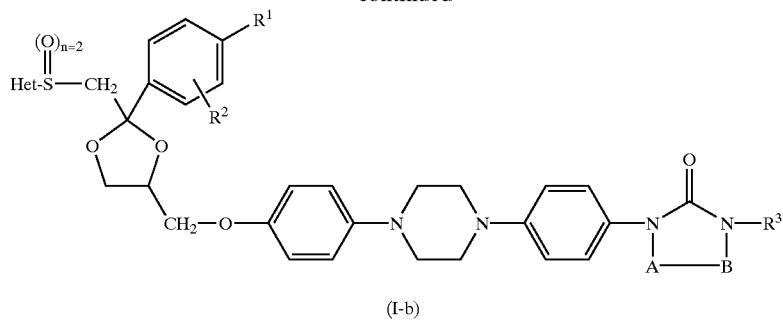

(I-b)

Also, compounds of formula (I) may be prepared starting from the art-known sulfide compound 4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one, or one or more of its stereoisomers, and S-oxidizing said compound using art-known methodologies. Depending on the amount of oxidizing agent and the reaction conditions the oxidation reaction may yield sulfoxides of formula (I-a) or sulfones of formula (I-b) or a mixture of both. Consequently, if a mixture of compounds of formula (I-a) and/or compounds of formula (I-b) is obtained, in case said mixture is a mixture of enantiomers, it can be separated by liquid chromatography using a suitable chiral stationary phase. Suitable chiral stationary phases are, for example, polysaccharides, in particular cellulose or amylose derivatives. Commercially available polysaccharide based chiral stationary phases are ChiralCel™CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. In case the mixture of compounds of formula (I-a) and/or compounds of formula (I-b) is a mixture of diastereomers then art known normal phase or reversed phase chromatography can be used.

S-oxidation reactions can be performed using a 30% aqueous solution of hydrogen peroxide, or by other oxidizing agents such as, $NaIO_4$, tert-butyloxychloride, acyl nitrites, sodium perborate and peracids. Sulfides can be oxidized to sulfoxides which can be further oxidized to sulfones by addition of another equivalent of hydrogen peroxide, $KMnO_4$, sodium perborate, potassium hydrogen persulfate or the like reagents. If enough oxidizing agent is present, sulfides can be converted directly to sulfones without isolation of the sulfoxides.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Depending upon the oxidizing agent and the reaction conditions both S-oxidation and N-oxidation can occur.

Intermediates of formula (III) can be prepared as described in Example A.1.

Intermediates of formula (II) can be prepared as described in Scheme 1. In Examples A.2 and A.3 intermediates of formula (II) are prepared according to said Scheme 1.

Scheme 1

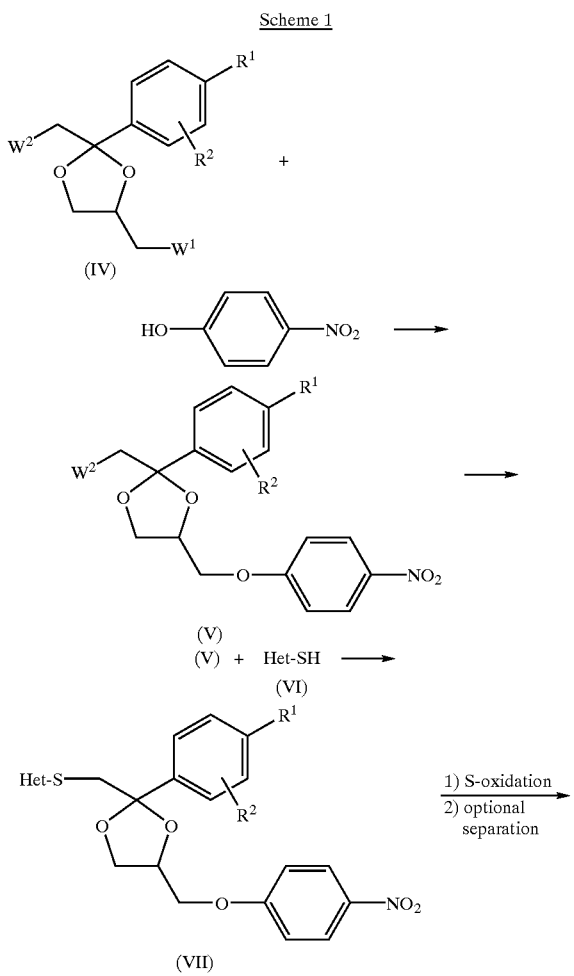

9

-continued

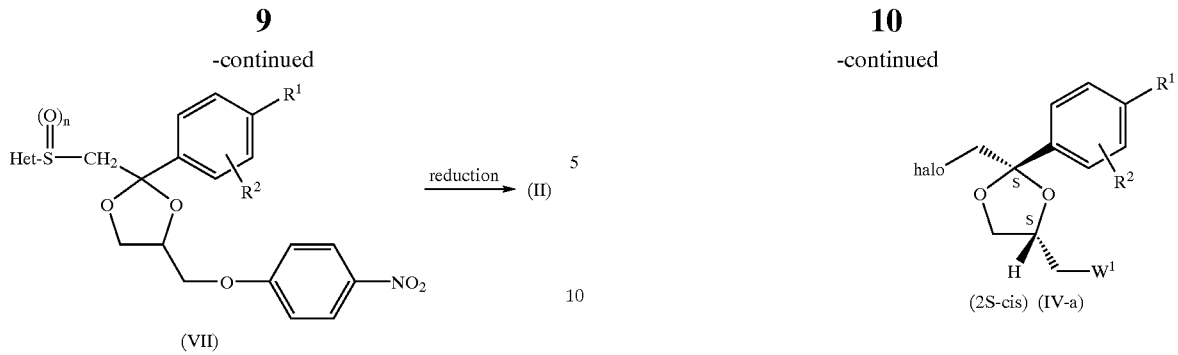

(VII)

In Scheme 1, intermediates of formula (IV), wherein $W^1$ and $W^2$ are each individually appropriate leaving groups such as, for example, halo, e.g. fluoro, chloro, bromo, iodo, or sulfonyloxy, e.g. methanesulfonyloxy, benzenesulfonyloxy, trifluoromethane-sulfonyloxy and the like reactive leaving groups are treated with p-nitrophenol and the resulting intermediates of formula (V) are then S-alkylated with an intermediate of formula (VI), yielding intermediates of formula (VII). Said intermediates (VII) are then S-oxidized using art-known methodologies into intermediates of formula (VIII) which are optionally separated into intermediates of formula (VIII) wherein n=1, said intermediates being represented by formula (VIII-a), and/or into intermediates of formula (VIII) wherein n=2, said intermediates being represented by formula (VIII-b).

Intermediates of formula (IV) having the cis-configuration and wherein $W^2$ is halo, said intermediates referred to as intermediates of formula (IV-a), can be prepared as depicted in scheme 2.

Scheme 2

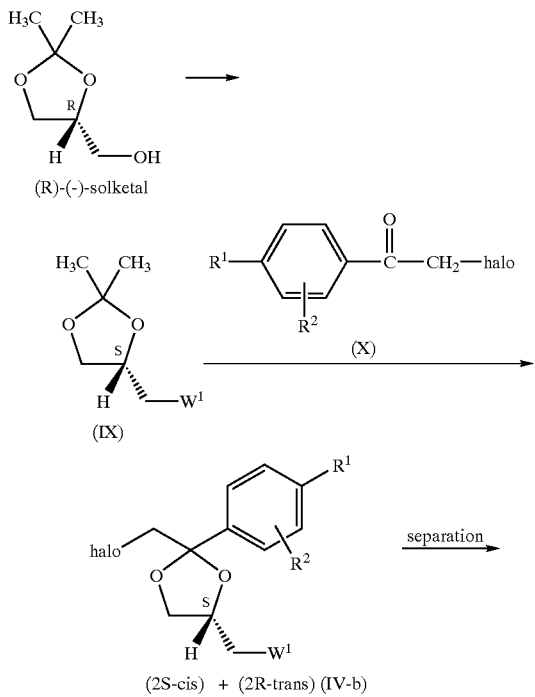

10

-continued

In scheme 2, the primary hydroxy group of (R)-(-)-solketal is converted into an appropriate leaving group $W^1$, wherein $W^1$ is defined hereinabove, thereby yielding intermediates of formula (IX) which are subsequently treated with an intermediate of formula (X). The resulting cis/trans mixture of intermediates of formula (IV-b), defined as intermediates of formula (IV) wherein $W^2$ is halo, can be separated into the intermediates of formula (IV-a) having the cis-configuration. In Examples A.6 and A.7 intermediates of formula (IV-a) are prepared according to said Scheme 2.

The starting materials and some of the intermediates are known compounds and are commercially available or may be prepared according to conventional reaction procedures generally known in the art. For example, intermediates of formula (IV) may be prepared according to art-known methodologies described in WO-96/13499.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Plasma levels of compounds 1, 2 and 3 and of compound A have been measured in a clinical trial on human volunteers. For a single 200 mg dose administration of compound A, it was found that for the total AUC (Area Under the Curve), said compound A accounted for only 8%, while compounds 1, 2 and 3 accounted for the remaining 92%. Taking into account the pharmacological activity of each compound, it was found that compound A made for only 28.6% of the total pharmacological activity while the compounds 1, 2 and 3 made up for the remaining 71.4%. Accordingly the compounds of the present invention have much higher plasma levels than compound A probably resulting from reduced metabolic breakdown and display a much larger pharmacological activity than compound A.

It was also found that clearance of the compounds 1, 2 and 3 is slower than clearance of compound A.

The compounds of formula (I), the N-oxide forms, the pharmaceutically acceptable salts and stereoisomeric forms thereof possess favourable apolipoprotein B inhibiting activity and concomitant lipid lowering activity. Therefore the present compounds are useful as a medicine especially in a method of treating patients suffering from hyperlipidemia, obesitas or atherosclerosis. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The causal relationship between hypercholesterolemia— particularly that associated with increased plasma concentrations of low density lipoproteins (LDL) and very low density lipoproteins (VLDL)—and premature atherosclerosis and cardiovascular disease is well established. VLDL is secreted by the liver and contains apolipoprotein B (apo-B); these particles undergo degradation in the circulation to LDL, which transports 60–70% of the total serum cholesterol. Apo-B is also the principal protein component of LDL. Increased LDL-cholesterol in serum, due to oversynthesis or decreased metabolism, is causally related to atherosclerosis. In contrast, high density lipoproteins (HDL) which contain apolipoprotein A1, have a protective effect and are inversely correlated with risk of coronary heart disease. The HDL/LDL ratio is thus a convenient method of assessing the atherogenic potential of an individual's plasma lipid profile.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesitas or atherosclerosis.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxy-propyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

Those of skill in the treatment of hyperlipidemia could easily determine the effective daily amount from the test results presented hereinafter. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.1 mg to 350 mg, and in particular 1 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

Experimental Part

In the procedures described hereinafter the following abbreviations were used: "ACN" stands for acetonitrile; "THF", which stands for tetrahydrofuran; "DCM" stands for dichloromethane; "DIPE" stands for diisopropylether; and "DMF" means N,N-dimethyl-formamide.

For some chemicals the chemical formula was used, e.g. $H_2$ for hydrogen gas, $N_2$ for nitrogen gas, $CH_2Cl_2$ for dichloromethane, $CH_3OH$ for methanol, $NH_3$ for ammonia, HCl for hydrochloric acid, and NaOH for sodium hydroxide.

In those cases the stereochemically isomeric form which was first isolated is designated as "A" and the second as "B", without further reference to the actual stereochemical configuration.

A. PREPARATION OF THE INTERMEDIATES

EXAMPLE A.1 a) Phenyl chloroformate (1.08 mol) was added dropwise at a temperature <20° C. to a stirring solution of 4-nitrobenzenamine (1.02 mol) in DMA (500 ml) on ice and the mixture was stirred overnight. The mixture was poured into water (1000 ml), stirred till a homogenously suspension and filtered off, yielding phenyl (4-nitrophenyl)carbamate (intermediate 1).

b) Hydrazine (1.18 mol) was added dropwise over a 1 hour period to a solution of intermediate (1) in 1,4-dioxane (1000 ml) and the mixture was stirred and refluxed overnight. The mixture was cooled and filtered off, yielding N-(4-nitro-phenyl)hydrazinecarboxamide (intermediate 2).

c) A mixture of intermediate (2) and methanimidamide acetate (2.4 mol) in 1-butanol (1500 ml) was stirred and refluxed for 5 hours and then stirred further for 48 hours. The precipitate was filtered off and washed with DIPE, yielding 48 g of 2,4-dihydro-4-(4-nitrophenyl) -3H-1,2,4-triazol-3-one (intermediate 3).

d) Reaction under argon atmosphere. A mixture of intermediate (3) (0.257 mol), (S)-1-methylpropanol methanesulfonate (ee of 82%) (0.282 mol) and sodium hydroxide (0.282 mol) in DMA (515 ml) was stirred vigorously for 6 hours at 60° C., then stood for 22 hours at room temperature. Water (350 ml) was added while stirring. Toluene (350 ml) was added while stirring. The biphasic mixture was stirred for 5 minutes. The layers were separated. The water layer was extracted with toluene. The combined organic layers were washed with water and with brine, dried, filtered and the solvent was evaporated, yielding a crude residue (90% (R) and 9% (S)). This crude residue was purified and separated into its enantiomers. Two pure fraction groups were collected and their solvent was evaporated, yielding 50.8 g of (R)-2,4-dihydro-2-(1-methylpropyl)-4-(nitrophenyl) -3H-1,2,4triazol-3-one (interm. 4) and 3.3 g of its (S)-enantiomer.

e) A mixture of intermediate (4) (0.19 mol) in THF (250 ml) and N,N-diethyl-ethanamine (20 ml) was hydrogenated at 50° C. with palladium on activated charcoal (2 g) as a catalyst in the presence of thiophene solution (1 ml) (2× the reaction mixture was filtered and fresh catalyst was added and hydrogenation was continued). After uptake of hydrogen (3 equivalents), the catalyst was filtered off over dicalite, and the filtrate was evaporated. The residue was stirred in boiling ACN, then heating was stopped and slowly HCl/2-propanol (35 ml) was poured into the mixture. Precipitation resulted. The mixture was stirred for 90 minutes, then stood for a while. The precipitate was filtered off by suction. The filtrate was evaporated. The residue was dissolved in warm ACN. HCl/2-propanol was added and the mixture was stood for 1 hour. The precipitate was filtered off by suction, washed with ACN, and air-dried at room temperature, yielding 21.28 g (41.7%) of (R)-4-(4-aminophenyl)-2,4-dihydro-2-(1-methylpropyl) -3H-1,2,4-triazol-3-one monohydrochloride (interm. 5).

f) Reaction under $N_2$ atmosphere. Intermediate (5) (0.075 mol) was dissolved in water (65 ml) and stirred vigorously for 30 minutes. $NH_4OH$ (0.15 mol) was added and the mixture was stirred vigorously for 10 minutes. Acetic acid (0.22 mol) was added. A solution of oxirane (0.750 mol) in water (85 ml) (prepared under cooling on an ice-bath) was poured into the mixture while cooling on ice. The reaction mixture was stirred for 2 hours on an ice-bath. The reaction mixture was cooled with ice (no water), and allowed to warm to room temperature in the melting ice-bath. The reaction mixture was stirred over the weekend at room temperature. Slowly, oxirane (gas) was bubbled through the mixture for 4–5 hours. The reaction mixture was stirred for 2 more hours.

During 15 minutes, more oxirane was bubbled through the mixture, while cooling on ice. The reaction mixture was stirred overnight at room temperature. Again, oxirane was added during 15 minutes. and the reaction mixture was stirred for 4 hours at room temperature. Then, DCM (200 ml) and 10 N NaOH (21 ml) were added and the mixture was stirred for 10 min. The organic layer was separated, washed with water and brine, dried, filtered and the solvent was evaporated. The residue (oil) was stirred in MIK (100 ml), cooled on ice and stirred for 15 minutes. The resulting precipitate was filtered off, washed with a minimal amount of MIK (2×) and with DIPE (1×50 ml), then air-dried at room temperature, yielding 18.6 g of (R)-4-[4-[bis(2-hydroxyethyl)-amino]phenyl]-2,4-dihydro-2-(1-methylpropyl)-3H-1,2,4-traizol-3-one (interm. 6). The filtrate was evaporated. The residue was stirred in a minimal amount of MIK, then cooled in ice and stirred for 60 minutes. The precipitate was filtered off, washed with a minimal amount of MIK, and once with DIPE, then air-dried at room temperature, yielding an additional amount of 2.3 g of intermediate (6).

g) Reaction under $N_2$ atmosphere. A solution of intermediate (6) (0.01 mol) in THF (15 ml) was stirred and cooled to −10° C. N,N-diethylethanamine (2.22 g) was added. A solution of methanesulfonyl chloride (0.022 mol) in TMF (10 ml) was added dropwise at −5° C. The reaction mixture was stirred for 35 minutes at −10/−5° C. The mixture was allowed to warm to 0°C. The reaction mixture was filtered cold over dicalite, rinsed with cold THF (20 ml) and the filtrate was evaporated, yielding a crude oil. This crude oil was dissolved in DCM (35 ml), stirred for 10 minutes with acetic acid (0.52 ml) in ice-water (30 ml) while cooling on an ice-bath. The organic layer was separated, washed with water and brine, dried, filtered and the solvent was evaporated, yielding 4.73 g of (R)-2,2'-[[4-[2,3-dihydro-2-(1-methylpropyl)-3-oxo-4H-1,2,4-triazol-4yl]phenyl]imino] diethanol bis(methanesulfonate) (ester) (99% , used in next reaction step, without further purification) (intern. 7).

EXAMPLE A.2 a) Reaction under argon atmosphere. A mixture of intermediate (18) (0.101 mol), 4-nitrophenol (0.101 mol) and NaOH (0.195 mol) in DMA (170 ml (DMA) was stirred for 16 hours at 90° C. The resulting reaction mixture was cooled on ice, water (170 ml) was added dropwise (precipitation resulted). The reaction mixture was stirred for 15 minutes on the cooling bath. The precipitate was filtered, washed with water and dried, yielding 31.55 g (73%) of (2S-cis)-2-bromomethyl-2-(4-chlorophenyl)4-[(4-nitrophenoxy) methyl]-1,3-dioxlane (interm 8).

b) Reaction under argon atmosphere. A mixture of intermediate (8) (0.075 mol), 4-methyl-4H-1,2,4-triazole-3-thiol (0.225 mol) and NaOH (0.225 mol) in DMA (150 ml) was stirred for 4 hours at 120° C., then stood overnight at room temperature, then re-heated to 50° C. and MIK (300 ml) was added. The temperature dropped to 40° C., and the mixture was warmed again to 50° C. Water (150 ml) was added. The resulting solution was warmed to 70° C. The underlying layer was removed with a pipette. The upper layer was washed twice with water (2×50 ml ; at 70° C). The remaining warm organic layer was stirred overnight at room temperature, then cooled for one hour on an ice-bath and the resulting precipitate was filtered off by suction, washed with 4 small, ice-cold portions of MIK (until a colorless filtrate was obtained) and the filter residue was rinsed twice with DIPE, then air-dried at room temperature, yielding 12.883 g of (2S-cis)-3-[[[2-(4-chlorophenyl)-4-[(4-nitrophenoxy) methyl-1,3-dioxolan-2-yl]methyl]-thio]-4-methyl-4H-1,2,4-triazole (interm. 9). The MIK filtrate was concentrated in vacuo. The concentrate was stirred and cooled on an ice-bath for 4 hours. The precipitate was filtered off by suction, washed with MIK (3×) and DIPE, then air-dried at room temperature, yielding an additional amount of 5.843 g of intermediate (9).

c) Intermediate (9) (0.0405 mol) was dissolved in DCM (240 ml), at room temperature. $NaHCO_3$ (0.0429 mol) was added in one portion. 3-Chlorobenzene-carboperoxoic acid (0.042 mol) was added in one portion (exothermic temperature rise to 30° C.). The reaction mixture was allowed to cool to room temperature and stirred for a while, resulting in formation of an oily supernatant and a precipitate. The reaction mixture was stood overnight at room temperature, then stirred for one hour at room temperature. A solution of $NaHSO_3$ (4.26 g) in water (350 ml) was added and the mixture was stirred for 15 minutes. The layers were separated. The organic layer was washed with water and brine (50% ), dried, filtered and the solvent was evaporated to give an oil.

This oil, i.e. [2S-[2α(A),4α]]+[2S-[2α(B),4α]]-3-[[[2-(4-chlorophenyl)-4-[(4nitrophenoxy)-methyl]-1,3-dioxolan-2-yl]methyl]sulfinyl]-4-methyl-4H-1,2,4-triazole (interm. 10), was dissolved in DCM (total volume: 160 ml). Intermediate (10) (¾ of said solution of 160 ml) was separated and purified by column chromatography over silica gel (eluent: ethyl acetate/$C_2H_5OH$ 100/0 to 98/2). Two pure fraction groups were collected and their solvent was evaporated, yielding 4.5 g of [2S-[2α(A),4α]]-3-[[[2-(4-chlorophenyl)-4-[(4-nitrophenoxy) methyl]-1,3-dioxolan-2-yl]methyl] sulfinyl]-4-methyl-4H-1,2,4-traizole (interm. 11) and 3 g (after crystallisation from methanol) of [2S-[2α(B),4α]]-3-[[[2-(4-chlorophenyl)-4-[(4-nitrophenoxy)-methyl]-1,3-dioxolan-2-yl]methyl]sulfinyl]-4-methyl-4H-1,2,4-triazole (interm. 12).

EXAMPLE A.3

A mixture of intermediate (10) (¼ of the solution of 160 ml), 3-chlorobenzene carboperoxoic acid (0.015 mol) and NaHCO$_3$ (0.0155 mol) in DCM (75 ml) was stirred for 20 hours at room temperature. More 3-chlorobenzenecarboperoxoic acid (0.0015 mol), NaHCO$_3$ (0.00155 mol) and DCM (25 ml) were added and the reaction mixture was stirred for 20 hours at room temperature. A solution of NaHSO$_3$ (1.715 g, 0.0165 mol) in water (100 ml) was added and the mixture was stirred for 20 minutes. The organic layer was separated, washed with water and brine, dried, filtered and the solvent was evaporated, yielding a crude residue. This crude residue was dissolved in DCM (100 ml). NaHCO$_3$ (0.005 mol) and 3-chlorobenzenecarboperoxoic acid (0.005 mol) were added and the reaction mixture was stirred for 5 hours at room temperature. Work-up: as above with adequate quantities, yielding a crude residue that was purified by column chromatography over silica gel (eluent : CH$_2$Cl$_2$/CH$_3$OH 98/2 and 95/5). The desired fractions were collected and the solvent was evaporated. The residue was dissolved in CH$_2$Cl$_2$, washed with 1 N NaOH, and the organic layer was separated, washed with water and brine, dried, filtered and the solvent was evaporated, yielding 3.6 g (72%) of (2S-cis)-3-[[[2-(4-chlorophenyl)-4-[(4-nitrophenoxy)methyl]-1,3-dioxolan-2-yl]methyl]sulfonyl]-4-methyl-4H-1,2,4-triazole (interm.13).

EXAMPLE A.4

In a 4-neck, 500-ml reaction flask, NH$_4$Cl (0.0856 mol) was stirred in water (86 ml) until complete dissolution. Fe powder (0.0515 mol) was added. Methanol (86 ml) was added and the mixture was stirred for 10 minutes at room temperature. Intermediate (11) (0.00858 mol) was added in portions over 10 minutes. The reaction mixture was heated to gentle reflux. The reaction mixture was stirred and refluxed for 135 minutes. At reflux, methanol (200 ml) was added and the mixture was stirred for 5 minutes. The mixture was filtered hot over dicalite. The reaction flask was flushed with hot methanol, and the filtrate was concentrated in vacuo. The aqueous concentrate was partitioned between water (100 ml) and CHCl$_3$ (250 ml). The layers were separated. The aqueous layer was re-extracted with CHCl$_3$ (100 ml). The combined organic layers were dried, filtered and the solvent was evaporated in vacuo. The residue was stood overnight under a gentle stream of nitrogen gas, yielding a crude residue that was purified by column chromatography over silica gel (eluent: CH$_2$Cl$_2$/CH$_3$OH 95/5). The pure fractions were collected and the solvent was evaporated, yielding 3.8 g (98.8%) of [2S-[2α(A),4α]]-4-[[2-(4-chlorophenyl)-2-[[(4-methyl-4H-1,2,4-triazol-3-yl)sulfinyl]-methyl]-1,3-dioxolan-4-yl]methoxy]benzamine (interm. 14). Analogously but starting from intermediate (12) [2S-[2α-[2α(B),4α]]-4-[[2-4-chlorophenyl)-2-[[(4-methyl-4H-1,2,4-triazol-3-yl)sulfinyl]-methyl]-1,3-dioxolan-4-yl-]methoxy]benzamine (interm. 15) was prepared.

EXAMPLE A.5

A mixture of intermediate (13) (0.0072 mol) in methanol (150 ml) was hydrogenated with platina on activated charcoal (2 g) as a catalyst in the presence of thiophene (2%) (1 ml). After uptake of hydrogen (3 equivalent), the catalyst was filtered off over dicalite and over a paper filter and the filtrate was evaporated, yielding 2.96 g (88%) of (2S-cis)-4-[[2-(4-chlorophenyl)-2-[[(4-methyl-4H-1,2,4-triazol-3-yl)sulfonyl]methyl]-1,3-dioxolan-4-yl]methoxy]benzenamine (interm. 16).

EXAMPLE A.6

To a solution of (4R)-2,2-dimethyl-1,3-dioxolane-4-methanol [or (R-)-(−)-solketal)] (134.8 g) in DCM (950 ml) triethylamine (170 ml) is added. The reaction mixture is cooled to 5° C. and mesylchloride (85.2 ml) is slowly added while keeping the temperature of the mixture below 10° C. After stirring for 1 hour, water (500 ml) is added and the resulting layers are separated. The organic layer is isolated and evaporated, yielding 220 g of (2S)-2,2-dimethyl-1,3-dioxolane-4-methanol methanesulfonate(ester) (intermediate 17).

EXAMPLE A.7

Intermediate (17) (52.3 g) is added to a solution of 2-bromo-4'-chloroacetophenone (59.5 g) in DCM (240 ml), followed by addition of methanesulfonic acid (15.4 ml). The reaction mixture is stirred for 2 hours at room temperature and an aqueous solution of Na$_2$CO$_3$ (10%, 250 ml) is added while stirring vigorously. The organic layer is isolated, washed with water (80 ml) and evaporated to dryness. The residue is dissolved in DCM (240 ml) and methanesulfonic acid (15.4 ml) is added. The reaction mixture is kept at room temperature for 18 hours, and an aqueous solution of Na$_2$CO$_3$ (10%, 250 ml) is added while stirring vigorously. The organic layer is isolated, washed with water (80 ml) and evaporated to dryness. The residue is very slowly crystallised from methanol, yielding 22.7 g of (2S-cis)-2-(bromomethyl)-2-(4-chlorophenyl)-1,3-dioxolane-4-methanol methanesulfonate(ester) (intermediate 18, $[\alpha]_D^{20}$= 23.46° (c=50.5 mg/5 ml in methanol)).

B. PREPARATION OF THE FINAL COMPOUNDS

EXAMPLE B.1

A mixture of intermediate (12) (0.003 mol), intermediate (7) (0.0033 mol) and N-(1-methylethyl)-2-propanamine (0.0077 mol) in tert-butanol (45 ml) was stirred for 12 hours at 80° C. The solvent was evaporated. The residue was dissolved in the eluent and purified by column chromatography over silica gel (eluent: CH$_2$Cl$_2$/hexane/CH$_3$OH 45/45/10 v/v). The pure fractions were collected and the solvent was evaporated in vacuo, yielding a crude residue that was crystallized from ethyl acetate, filtered off and dried, yielding 1.17g (52%) of [2S-[2α,4α(S*)]]-4-[4-[4-dioxolan-4-yl]methoxy]phenyl]-1-piperazinyl]phenyl]-2,4-dihydro-2-(1-methylpropyl)-3H-1,2,4-triazol-3-one; $[\alpha]_D^{20}$ −32.05° (c=0.5% in DMF) (compound 1).

EXAMPLE B.2

A mixture of intermediate (14) (0.003 mol), intermediate (7) (0.0033 mol) and N-(1-methylethyl)-2-propanamine (0.0077 mol) in tert-butanol (45 ml) was stirred for 12 hours at 80° C. The solvent was evaporated. The residue was dissolved in the eluent and purified by column chromatography over silica gel (eluent: CH$_2$Cl$_2$/hexane/CH$_3$OH 45/45/10 v/v). The pure fractions were collected and the solvent was evaporated, yielding a crude residue that was triturated under hot diethyl ether, then cooled to room temperature and the resulting precipitate was filtered off and dried, yielding 0.977 g (44%) of [2S-[2α(A),4α(S*)]]-4-[4-[4-[4-[[2-(4-chlorophenyl)-2-[[(4-methyl-4-H-1,2,4triazol-3-yl)sulfinyl]methyl]-1,3-dioxolan-4-yl]methyl]phenyl]-1-piperazinyl]phenyl]-2,4-dihydro-2-(1-methylpropyl) 3H-1,2,4-traizol-3-one (compound 2; $[\alpha]_D^{20}$ −60.45° (c=24.73 mg/5 ml DMF).

EXAMPLE B.3

A mixture of intermediate (15) (0.003 mol), intermediate (7) (0.0033 mol) and N-(1-methylethyl)-2-propanamine (0.0077 mol) in tert-butanol (45 ml) was stirred for 12 hours at 80° C. (oil bath), then allowed to cool to room temperature. The solvent was evaporated. The residue was partitioned between chloroform (200 ml) and water (100 ml) stirred for 5 minutes and the layers were separated. The organic layer was washed with water and brine, dried, filtered and the solvent was evaporated. The residue was purified by column chromatography over silica gel (eluent : $CH_2Cl_2$/n-hexane/$CH_3OH$ 45/45/10). The desired fractions were collected and the solvent was evaporated. The residue was suspended in hot ethyl acetate, then allowed to cool to room temperature, filtered off by suction, washed with ethyl acetate and dried, yielding 0.900 g (41%) of [2S-[2α(B),4α(S*)]]-4-[4-[4-[4-[[2-(4-chlorophenyl)-2-[[(4-methyl-4H-1,2,4-traizol-3yl]sulfinyl]methyl]-1,3-dioxolan-4-yl]methoxy]phenyl]-1-piperazinyl]Phenyl-2,4-dihydro-2-(1-methylpropyl)-3H-1,2,4-traizol-3-one (compound 3).

Table F-1 list the compounds that were prepared according to one of the above Examples.

istry and Physics of Lipids, 38, 205–222 (1985). To prepare the donor and acceptor vesicles, the appropriate lipids in chloroform were put into a glass test tube and dried under a stream of $N_2$. A buffer containing 15 mM Tris-HCl pH 7.5, 1 mM EDTA, 40 mM NaCl, 0.02% $NaN_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri [1-$^{14}C$]-oleate), acceptor vesicles (240 nmol phosphatidylcholine) and 5 mg BSA in a total volume of 675 μl in a 1.5 ml microcentrifuge tube. Test compounds were added dissolved in DMSO (0.13% final concentration). After 5 minutes of pre-incubation at 37° C., the reaction was started by the

TABLE 1

| Co. No. | n | Chemical Abstracts stereodescriptors | Physical data |
|---|---|---|---|
| 1 | 2 | [2S-[2α,4α(S*)]] | $[α]_D^{20}$ = −32.05° (c = 0.5% in DMF) |
| 2 | 1 | [2S-[2α(A),4α(S*)]] | $[α]_D^{20}$ = −60.45° (c = 24.73 mg/5 ml DMF) |
| 3 | 1 | [2S-[2α(B),4α(S*)]] | — |
| 4 | 1 | [R*(2A*),R*] | — |
| 5 | 1 | [R*(2A*),S*] | — |
| 6 | 1 | [R*(2B*),R*] | — |
| 7 | 1 | [R*(2B*),S*] | — |
| 8 | 1 | [R*(2A*),S*(4R)] | — |
| 9 | 1 | [R*(2A*),R*(4R)] | — |
| 10 | 1 | [R*(2A*),S*(4S)] | — |
| 11 | 1 | [R*(2A*),R*(4S)] | — |

C. PHARMACOLOGICAL EXAMPLES

C.1. Quantification of the Secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 min at 1320 g and washed twice with a buffer containing 40 mM Mops, 40 mM $NaH_2PO_4$, 100 mM NaF, 0.2 mM DTT, 5 mM EDTA, 5 mM EGTA, 1% Triton-X-100, 0.5% sodium deoxycholate (DOC), 0.1% SDS, 0.2 μM leupeptin and 0.2 μM PMSF. Radioactivity in the pellet was quantified by liquid scintillation counting. Resulting $IC_{50}$ values are enumerated in Table C. 1.

C.2 MTP Assay

MTP activity was measured using an assay similar to one described by J. R. Wetterau and D. B. Zilversmit in *Chem-* addition of MTP in 100 μl dialysis buffer. The reaction was stopped by the addition of 400 μl DEAE-52 cellulose pre-equilibrated in 15 mM Tris-HCl pH 7.5, 1 mM EDTA, 0.02% $NaN_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}C$]-counts were used to calculate the percent triglyceride transfer from donor to acceptor vesicles. Resulting $IC_{50}$ values are enumerated in Table C.1.

TABLE C.1

$IC_{50}$ values for Examples C.1 and C.2

| Compound | ApoB secretion $IC_{50}$ (nM)[b] | Dog MTP activity $IC_{50}$ (nM)[a] |
|---|---|---|
| compound A | 25 | 7.6 |
| 1 | 61 | 6.2 |
| 2 | 930 | 118 |
| 3 | 94 | 11 |

[a]$IC_{50}$ values are the drug concentrations that correspond with the 50% of control values in FIG. 2..
[b]$IC_{50}$ values were calculated by non-linear regression analysis

What is claimed is:

1. A compound of formula (I)

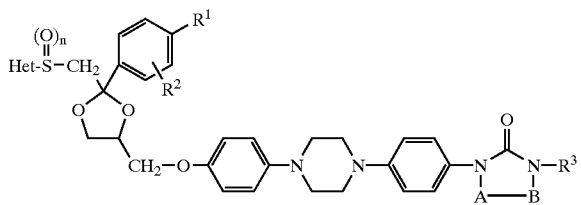

the N-oxides, the stereochemically isomeric forms thereof, and the pharmaceutically acceptable acid addition salts, wherein n is 1 or 2;
$R^1$ is hydrogen, $C_{1-6}$alkyl or halo;
$R^2$ is hydrogen or halo;
$R^3$ is $C_{1-8}$alkyl or $C_{3-6}$cycloalkyl;
Het is a radical of formula

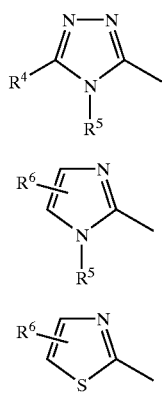

wherein
$R^4$ is hydrogen, $C_{1-4}$alkyl, trifluoromethyl, amino or hydroxy;
$R^5$ is hydrogen or $C_{1-4}$alkyl;
$R^6$ is hydrogen or $C_{1-4}$alkyl; and
—A—B— is a bivalent radical of formula —CH=CH— (b-1)
—N=CH— (b-2)
—CH=N— (b-3)

wherein optionally one of the hydrogen atoms is replaced by $C_{1-4}$alkyl.

2. A compound as claimed in claim 1 wherein the bivalent radical —A—B— is a radical of formula —CH=N— (b-3).

3. A compound as claimed in claim 1 wherein $R^1$ is halo, $R^2$ is hydrogen, $R^3$ is $C_{1-4}$alkyl and Het is a radical of formula (a-1) wherein $R^4$ is hydrogen and $R^5$ is $C_{1-4}$alkyl.

4. A compound as claimed in claim 1 wherein the dioxolane moiety has the (2S-cis) configuration.

5. A compound according to claim 1 wherein the compound is

[2S-[2α,4α(S*)]]-4-[4-[4-[4-[[2-(4-chlorophenyl)-2-[[(4-methyl-4H-1,2,4-triazol-3-yl)sulfonyl]methyl]-1,3-dioxolan-4-yl]methoxy]phenyl]-1-piperazinyl]phenyl]-2,4-dihydro-2-(1-methylpropyl)-3H-1,2,4-triazol-3-one;

[2S-[2α(A),4α(S*)]]-4-[4-[4-[4-[[2-(4-chlorophenyl)-2-[[(4-methyl-4H-1,2,4-triazol-3-yl)sulfinyl]methyl]-1,3-dioxolan-4-yl]methoxy]phenyl]-1-piperazinyl]phenyl]-2,4-dihydro-2-(1-methylpropyl)-3H-1,2,4-triazol-3-one; and

[2S-[2α(B),4α(S*)]]-4-[4-[4-[4-[[2-(4-chlorophenyl)-2-[[(4-methyl-4H-1,2,4-triazol-3-yl)sulfinyl]methyl]-1,3-dioxolan-4-yl]methoxy]phenyl]-1-piperazinyl]phenyl]-2,4-dihydro-2-(1-methylpropyl)-3H-1,2,4-triazol-3-one; or a pharmaceutically acceptable acid addition salt thereof.

6. A pharmaceutical composition comprising a pharmaceutically acceptable carrier and a therapeutically active amount of a compound as claimed in claim 1.

7. A process for preparing a pharmaceutical composition wherein a therapeutically active amount of a compound as claimed in claim 1 is intimately mixed with a pharmaceutically acceptable carrier.

8. A process for preparing a compound of formula (I) wherein a) an intermediate of formula (II) is reacted with an intermediate of formula (III) in a reaction-insert solvent and, optionally in the presence of a suitable base,

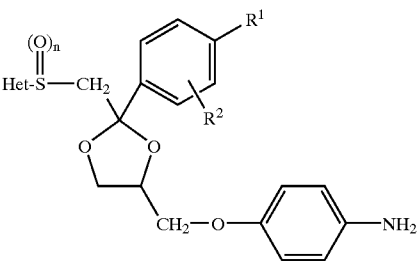   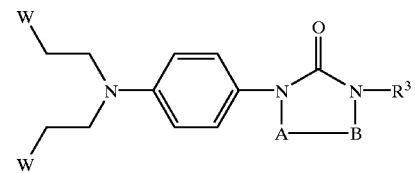

wherein in the above reaction scheme W is an appropriate leaving group and n is 1 or 2;

b) compounds of formula (I-a), defined as compounds of formula (I) wherein n=1, are S-oxidized to compounds of formula (I-b), defined as compounds of formula (I) wherein n=2,

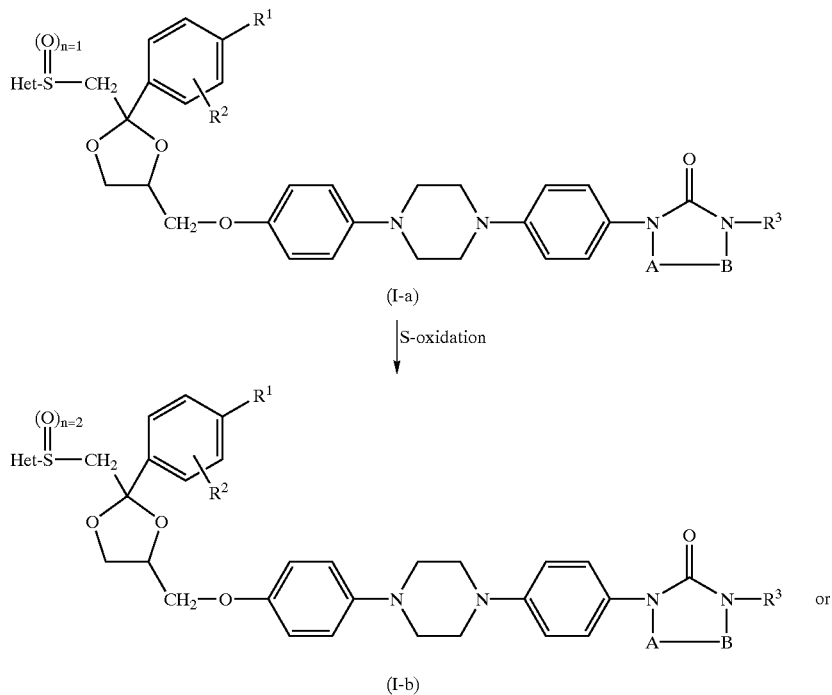

c) if desired, a compound of formula (I) is converted into an acid addition salt, or conversely, an acid addition salt of a compound of formula (I) is converted into a free base form with alkali.

9. A method of treating a patient suffering from hyperlipidemia, obesitas, or atherosclerosis comprising administering to said patient a therapeutically effective amount of a compound as claimed in claim 1.

* * * * *